(12) United States Patent
Pancallo

(10) Patent No.: US 6,193,513 B1
(45) Date of Patent: Feb. 27, 2001

(54) DENTAL DEVICE ACTING AS A VARIABLE-HEIGHT MOUTH OPENER, A SALIVA EJECTOR AND AN ORAL DAM

(76) Inventor: Renato Pancallo, Via Piromali 23, 89048 Siderno Marina, Reggio Calabria (IT)

( * ) Notice: Subject to any disclaimer, the term of this patent is extended or adjusted under 35 U.S.C. 154(b) by 0 days.

(21) Appl. No.: 09/309,414

(22) Filed: May 10, 1999

(30) Foreign Application Priority Data

May 20, 1998 (IT) .............................. MI980358 U

(51) Int. Cl.[7] .................................................. A61C 17/06
(52) U.S. Cl. .................................................. 433/93; 433/140
(58) Field of Search ............................ 433/93, 94, 138, 433/140

(56) References Cited

U.S. PATENT DOCUMENTS

| | | | |
|---|---|---|---|
| 4,215,984 | 8/1980 | Reichley | 433/93 |
| 4,992,046 * | 2/1991 | Sharp | 433/93 |
| 5,516,286 * | 5/1996 | Kushner | 433/93 |

FOREIGN PATENT DOCUMENTS

| | | | |
|---|---|---|---|
| 2347918 | 11/1977 | (FR) | A61C/3/00 |

* cited by examiner

Primary Examiner—John J. Wilson
Assistant Examiner—Melba Bumgarner
(74) Attorney, Agent, or Firm—Steinberg & Raskin, P.C.

(57) ABSTRACT

Dental device acting as a variable-height mouth opener, a saliva ejector and an oral dam including a casing having a shape reproducing the shape of the dental arches and able to maintain the patient's mouth open once inserted into it in contact with the dental arches, and a saliva discharge opening communicating with a tube for removing the saliva by suction applied to the other end of the tube. The size of the device casing in the mastication direction can be varied from a minimum to a maximum, for example, by pivotally mounting a projecting element to the casing.

20 Claims, 2 Drawing Sheets

DENTAL DEVICE ACTING AS A VARIABLE-HEIGHT MOUTH OPENER, A SALIVA EJECTOR AND AN ORAL DAM

FIELD OF THE INVENTION

The present invention relates to a dental device acting simultaneously as a mouth opener, an oral dam and a saliva ejector.

BACKGROUND OF THE INVENTION

A dental instrument of this type is already known from Italian Patent Application No. RC94U 000011, which has the same inventor as the present application. This instrument comprises:

- a casing having a shape reproducing the shape of the dental arches and able to maintain the patient's mouth open once inserted into it in contact with the dental arches; and
- a saliva discharge opening communicating with a tube for removing the saliva by suction applied to the other end of the tube.

The aforedescribed instrument is conveniently provided with means for coupling the instrument to the patient's teeth in order to maintain the instrument in position relative to the patient's mouth.

Using such an instrument, it has been found that although being very useful in achieving sufficient opening of the patient's mouth, its casing is too bulky in the mastication direction, so that it is uncomfortable to insert into the patient's mouth.

Moreover, because of its size in mastication direction, the known dental instrument does not leave sufficient space free for the dentist to carry out the operations required within the patient's mouth with ease.

OBJECTS AND SUMMARY OF THE INVENTION

Accordingly, it is an object of the present invention to provide a device of the aforesaid type which avoids the above-mentioned drawbacks of the instrument disclosed in Italian Patent Application No. RC94U 000011, i.e., it does not have a casing which is bulky in the mastication direction and therefore it is not uncomfortable to insert into the patient's mouth, and leaves sufficient space free for the dentist to operate in the patient's mouth.

Another object of the present invention is to provide a new and improved dental device acting as a variable-height mouth opener, a saliva ejector and an oral dam.

In order to attain these objects and others, a dental device in accordance with the invention comprises means for varying the size of the device casing in the mastication direction from a minimum to a maximum. In this manner, the device casing can be easily inserted into the patient's mouth when in its minimum size state, after which, the casing can be made to assume its maximum size in the mastication direction.

Further, to provide for sufficient space for the dentist to operate in the patient's mouth, the device has a casing of reduced size in the mastication direction and from the casing, once inserted into the patient's mouth, an element having transverse dimensions substantially smaller than the transverse dimensions of the casing itself is able to project towards the palate until it makes contact with the palate. This projecting element is lockable in its projecting position. In this manner, a considerable free space occupied only by the projecting element remains between the casing and palate.

Conveniently, the free end of the projecting element is shaped to adapt to the shape of the palate region with which it is intended to make contact.

Preferably, the casing is hollow and open at the insertion end for the patient's tongue so that this can enter the casing.

In one particular embodiment, the dental device comprises a casing having a shape reproducing the shape of dental arches and adapted to maintain the patient's mouth open once inserted into the patient's mouth and in contact with the dental arches, the casing including a saliva discharge opening adapted to receive a tube for removing saliva from the patient's mouth by suction applied to an end of the tube, and engaging means coupled to the casing for selectively engaging a palate of the patient's mouth and thereby secure the casing in the patient's mouth. The engaging means comprise a projecting element having a first end and a second end and is movable between a first position in which the first end is situated in the casing and the second end is exterior of the casing and a second position in which the first end is situated exterior of the casing and the second end is situated in the casing. When the first end is exterior of the casing, the casing has a larger size in the mastication direction then when the first end is situated in the casing. The projecting element may be lockable in the second position, e.g., by locking means, and may also be sickle-shaped and lie substantially in a vertical plane. In the latter case, a horizontal pin pivotally mounts the projecting element to the casing at an intermediate point and the casing comprises a slit in a front face through which the first end of the projecting element projects when in the second position. thus, the locking means may entail the slit comprising two notches and a wedge adapted to be inserted into one of the notches to lock the projecting element in a position of maximum projection of the first end.

The invention will be described in detail with reference to some preferred embodiments of the invention illustrated in the figures in the accompanying drawing. However, the invention is not confined to the illustrated embodiments alone.

BRIEF DESCRIPTION OF THE DRAWINGS

Additional objects of the invention will be apparent from the following description of the preferred embodiment thereof taken in conjunction with the accompanying non-limiting drawings, in which.

DETAILED DESCRIPTION OF THE PREFERRED EMBODIMENTS

Figure 1:
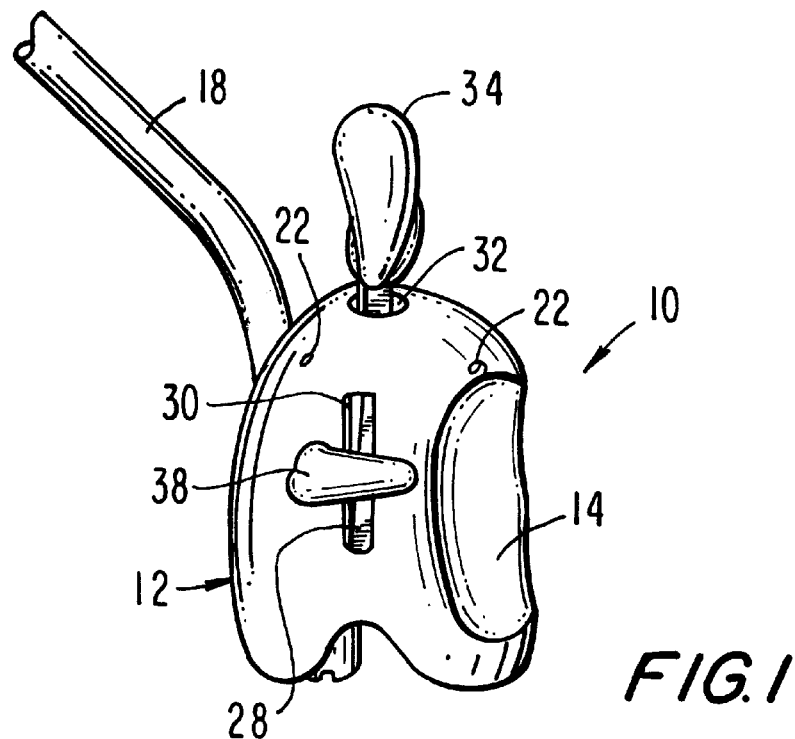
FIG. 1 is a front perspective view of the device in accordance with the invention in its condition of maximum size in the mastication direction.

Referring to FIGS. 1–4 wherein like reference numerals refer to the same or similar elements, a dental device in accordance with the invention is designated generally as 10 and comprises a casing 12 of non-traumatic material, such as a plastic material suitable for the use for which it is intended, or a suitable rubber, which must however be fairly rigid. The casing 12 has an outer shape which roughly reproduces the shape of the dental arches and, in this specific case, is hollow and open both to the rear and downwards, with the advantage that the internal cavity of the casing 12 can accommodate the patient's tongue.

Figure 2:
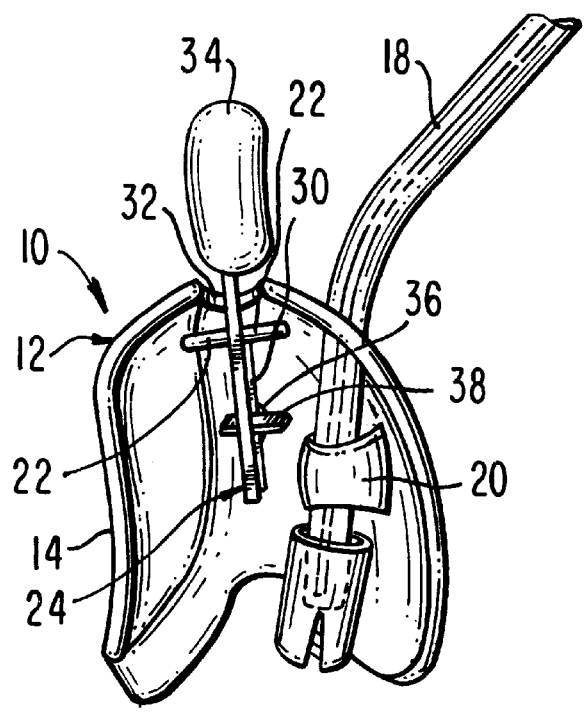
FIG. 2 is a rear perspective view of the device in accordance with the invention.

As can be seen in particular from FIGS. 1 and 2, the casing 12 is not symmetrical but rather includes an external concavity 14 in its right side (see FIG. 1). This is because the relative device has been designed for the case in which the patient's left dental semi-arch is to be operated upon, the concavity 14 hence providing greater operating space in the relative region. Likewise, the device of the invention can be given a shape similar to that of the illustrated casing 12, if the patient's right dental semi-arch is to be operated upon.

Figure 3:
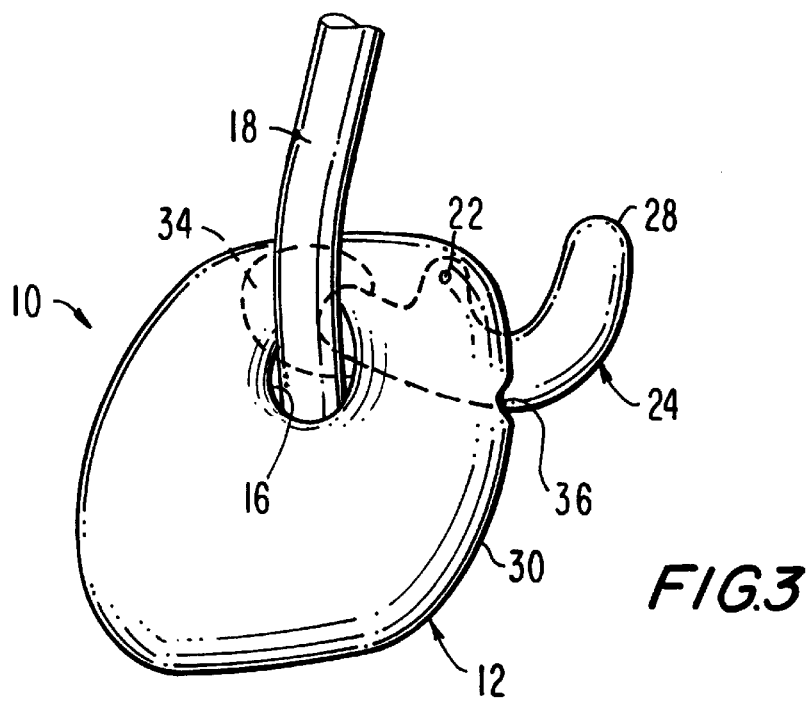
FIG. 3 is a perspective right side view of the device in accordance with the invention when in its state of minimum size in the mastication direction
Figure 3A:
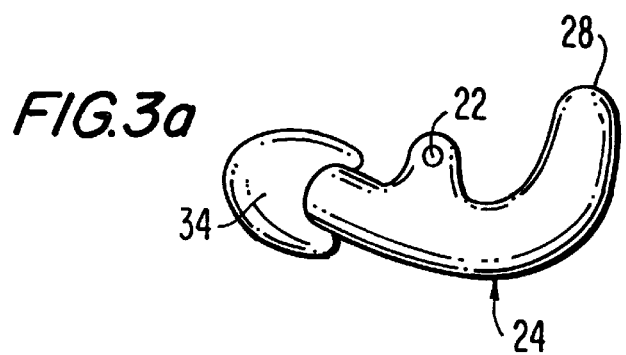
FIG. 3a is a perspective view of the sickle element as seen in FIG. 3.
Figure 4:
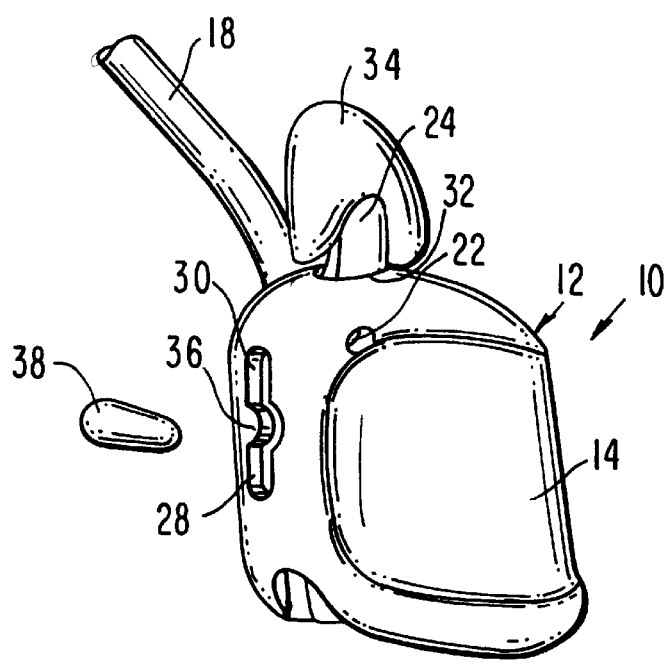
FIG. 4 is a perspective left side view of the device in accordance with the invention when in its maximum size state.

Returning to the embodiment shown in FIGS. 1–4, it can be seen in particular from FIG. 3 that in the right side of the casing 12 there is provided a through hole 16 enabling one end of a saliva ejector tube 18 to be inserted into the casing 12, its other end being connected to a usual vacuum source. As can be seen from FIG. 2, the tube 18 is retained by a sleeve 20 fixed to the inner wall of the casing 12.

A projecting element, such as a connecting rod or sickle element 24, is rotatably fixed to the casing 12 by a horizontal pin 22 at an intermediate point, to thereby be able to rotate in a vertical plane. As can be seen from FIGS. 3 and 4, as well as lying in a vertical plane, the sickle element 24 has a first end 28 projecting from a vertical slit 30 (FIGS. 1 and 4) provided in the front of the casing 12. The other end of the sickle element 24 can project from a rearwardly open aperture 32 (FIGS. 1 and 2) provided in the top of the casing 12. On the end of the sickle element 24, there is fixed a counteracting element or cap 34 of the same material as the casing 12. The sickle element 24 can assume two different angular positions, namely a first position (visible in FIG. 3) in which the first end 28 of the sickle 24 projects considerably from the casing 12 via the slit 30, whereas the second end of the sickle 24, including the cap 34, does not project from the casing 12, and a second position in which the first end 28 of the sickle 24 does not project from the casing 12 (however in FIG. 1 this is not shown distinctly), whereas the second end on which the cap 34 is fixed projects considerably from it.

In correspondence with the vertical slit 30, the casing 12 comprises on its front face two special notches, of which one of these, indicated by 36, can be seen in FIG. 3. A wedge 38 can be inserted into these notches to lock the sickle element 24 in its most projecting position. Instead of the notches 36 and wedge 38, other means can be provided to lock the second end of the sickle element 24 in its projecting position.

It should also be noted that besides comprising a right or left concavity 14, the described dental device can be constructed in various sizes to enable each patient to use the most suitable device.

A brief description will now be given of the method of using the described device 10. The device 10 is positioned in the patient's mouth such that the convex front surface of the casing 12 (that visible in FIG. 1) faces the inner surface of the patient's incisors, whereas its upper face (that from which the cap 34 can project upwards), also convex, faces the patient's palate. The roughly U-shaped lower edge of the casing 12 hence makes contact with the floor of the patient's mouth. As shown seen in FIGS. 1, 2 and 3, this edge comprises in its front an incisure to prevent trauma to the caruncle of the tongue. Before inserting the casing 12 into the patient's mouth, it must be checked that the sickle 24 lies in the angular position shown in FIG. 3, so that insertion can take place without any difficulty., i.e., the device has the minimum transverse dimension to facilitate insertion into the patient's mouth.

As already stated, as the casing 12 has a concavity or depression 14 on the right (with reference to FIG. 1), it is suitable for operating on the patient's left dental semi-arch. If it is required to operate on the right dental semi-arch a casing is used which is mirror-image to the casing 12 (i.e., in which the concavity is on the left, again with reference to FIG. 1).

After positioning the casing 12 in the patient's mouth, the first end 28 of the sickle 24 is pressed with one finger so that this end totally enters the casing 12, i.e., is situated in the casing 12. This makes the cap 34 project upwards out of the casing 12, to lie as in FIGS. 1, 2 and 4. At this point, the wedge 38 is inserted into the notches 36 to lock the sickle 24 in position. Consequently, the patient can no longer close his mouth. Upon removal of the wedge 38, the cap 34 can be made to re-enter the casing 12, enabling the casing 12 to be easily extracted from the patient's mouth.

As will be easily apparent the dental device of the invention facilitates the dentist's work in that:

it allows the field of operation to be totally isolated thereby preventing interference by the tongue and ingress of saliva, the device acting as a barrier interposed between the teeth and the mouth cavity;

it maintains the patient's mouth open, hence acting as a mouth opener;

it enables saliva to be drawn off to provide a dry field of operation, hence acting as a saliva ejector;

it provides improved vision of the field of operation; and it can be quickly put in place.

Above, some preferred embodiments of the invention have been described, and it is obvious to a person skilled in the art that numerous modifications can be made to these embodiments within the scope of the inventive idea defined in the accompanying patent claims. As such, the examples provided above are not meant to be exclusive. Many other variations of the present invention would be obvious to those skilled in the art, and are contemplated to be within the scope of the appended claims.

I claim:

1. A dental device comprising:

a casing structured and arranged to be completely inserted within an oral cavity of a patient having a shape reproducing the shape of dental arches having a front face for contacting the patient's incisors, an upper face for contacting the patient's palate and a lower edge for contacting the floor of the patient's mouth, the casing being adapted to maintain the patient's mouth open once inserted into the patient's mouth and in contact with the dental arches, said casing including a saliva discharge opening adapted to receive a tube for removing saliva from the patient's mouth by suction applied to an end of the tube, and means coupled to said casing for varying a size of the device in a mastication direction from a minimum in which said casing can be inserted into the patient's mouth to a maximum in which the means coupled to said casing forces the patient's mouth open by pressing against the patient's palate whereby the patient is prevented from closing their mouth.

2. The device of claim 1, wherein said means for varying the size of said casing comprise
a projecting element having a first end structured and arranged to project from a front of said casing and an opposite end structured and arranged to project from a top of said casing, said projecting element being rotatably coupled to said casing and having a first position in which said first end projects from the front of said casino whereby said casing has a reduced size in the mastication direction and a second position in which said opposite end of said projecting element projects from the top of said casing whereby a transverse dimension of said casing is enlarged, said projecting element having transverse dimensions substantially smaller than transverse dimensions of said casing.

3. The device of claim 2, wherein said projecting element is lockable in said second position.

4. The device of claim 2, wherein said opposite end of said projecting element has a shape structured and arranged to engage a palate region of the patient's mouth.

5. The device of claim 2, wherein said projecting element is substantially sickle-shaped and lies substantially in a vertical plane, further comprising
a horizontal pin for pivotally mounting said projecting element to said casing at an intermediate point,
said casing comprises a slit in a front face,
the projecting element being in said first position when the first end of said projecting element projects from said slit and the opposite end of said projecting element is contained within said casing, and the projecting element being in said second position when said opposite end projects above the top of said casing, said projection of said opposite end being a maximum when said first end does not project or projects only slightly from said casing.

6. The device of claim 5, wherein said slit further comprises two notches and
a wedge adapted to be inserted into one of said notches to lock said projecting element in the position of maximum projection of said opposite end by preventing the first end from projecting out of said slit.

7. The device of claim 2, further comprising locking means for locking said projecting element in said second position.

8. The device of claim 2, wherein said projecting element is pivotally mounted to said casing for rotation between said first and second positions.

9. The device of claim 1, wherein said casing has a lateral concavity in a side.

10. The device of claim 9, wherein said casing comprises an aperture through which the tube is insertable, said aperture being situated in a side of said casing opposite to the side in which said concavity is provided.

11. The device of claim 1, wherein said casing comprises an aperture through which the tube is insertable.

12. The device of claim 1, wherein said casing and said means for varying the size of said casing are made of a non-traumatic material.

13. The device of claim 1, further comprising a sleeve arranged on an interior surface of said casing for retaining the tube.

14. A dental device comprising
a casing structured and arranged to be completely inserted within an oral cavity of a patient having a shape reproducing the shape of dental arches having a front face for contacting the patient's incisors, an upper face for contacting the patient's palate and a lower edge for contacting the floor of the patient's mouth, the casing being adapted to maintain the patient's mouth open once inserted into the patient's mouth and in contact with the dental arches, said casing including a saliva discharge opening adapted to receive a tube for removing saliva from the patient's mouth by suction applied to an end of the tube, and
engaging means coupled to said casing for selectively engaging a palate of the patient's mouth and thereby secure said casing in the patient's mouth.

15. The device of claim 14, wherein said engaging means comprise
a projecting element having a second end and a first end and being movable between a first position in which said second end is situated in said casing and said first end is exterior of said casing and a second position in which said second end is situated exterior of said casing and said first end is situated in said casing, when said second end is exterior of said casing, said casing having a larger size in the mastication direction then when said second end is situated in said casing.

16. The device of claim 15, wherein said projecting element is lockable in said second position.

17. The device of claim 15, wherein said projecting element is substantially sickle-shaped and lies substantially in a vertical plane, further comprising
a horizontal pin for pivotally mounting said projecting element to said casing at an intermediate point,
said casing comprises a slit in a front face through which said first end of said projecting element projects when in said first position.

18. The device of claim 17, wherein said slit comprises two notches, further comprising:
a wedge adapted to be inserted into one of said notches to lock said projecting element in a position of maximum projection of said second end.

19. The device of claim 15, further comprising locking means for locking said projecting element in said second position.

20. The device of claim 15, wherein said projecting element is pivotally mounted to said casing for rotation between said first and second positions.

* * * * *